United States Patent [19]
Anderson et al.

[11] Patent Number: 5,306,468
[45] Date of Patent: Apr. 26, 1994

[54] APPARATUS FOR THE HANDLING OF ELECTROPHORETIC TRANSFER MEMBRANES AND FOR THE CHEMILUMINESCENT DETECTION OF BLOTS CONTAINED THEREON

[75] Inventors: Lynne E. Anderson; Robert K. Kobos, both of Wilmington, Del.; Shay E. Polsky, West Chester, Pa.; Charles W. Robertson, Rockland, Del.

[73] Assignee: E. I. Du Pont de Nemours and Company, Wilmington, Del.

[21] Appl. No.: 739,123

[22] Filed: Jul. 19, 1991

[51] Int. Cl.$^5$ ................................ B01L 9/00
[52] U.S. Cl. .................. 422/101; 204/182.8; 422/99; 422/104
[58] Field of Search .............. 422/99, 101, 104; 204/182.8; 100/93 P

[56] References Cited

U.S. PATENT DOCUMENTS

| | | | |
|---|---|---|---|
| Re. 30,595 | 4/1981 | Covington et al. | 422/63 |
| 4,152,390 | 5/1979 | Nosco et al. | 422/63 |
| 4,589,965 | 5/1986 | Kreisher | 204/182.8 |
| 4,705,847 | 11/1987 | Hummelen et al. | 530/350 |
| 4,812,216 | 3/1989 | Hurd et al. | 204/182.8 |
| 4,857,652 | 8/1989 | Schaap | 549/510 |
| 4,874,492 | 10/1989 | Mackay | 204/299 R |
| 4,913,791 | 4/1990 | Hurd et al. | 204/299 R |
| 4,931,223 | 6/1990 | Bronstein | 436/537 |
| 4,948,975 | 8/1990 | Erwin et al. | 250/361 |
| 4,952,707 | 8/1990 | Edwards et al. | 549/221 |
| 4,956,477 | 9/1990 | Bronstein et al. | 549/221 |
| 4,959,182 | 9/1990 | Schaap | 252/700 |
| 5,155,049 | 10/1992 | Kauvar et al. | 422/101 X |

OTHER PUBLICATIONS

Bronstein et al., J. Biolumin, Chemilumin., 4, 99-111 (1989).
Kiel, Bioelectromagnetics 4, 193-204 (1983).

Primary Examiner—Jill A. Johnston

[57] ABSTRACT

Improved apparatus for the handling and detecting of an electrophoretic transfer membrane is disclosed herein, the improvement comprising guide apparatus designed to accommodate the transfer membrane, a pressure head positioned relative to the guide apparatus to releasably engage the membrane, and light shielding apparatus positioned relative to the guide apparatus to selectively enclose about the transfer membrane. The apparatus is operated so that the pressure head engages a flexible portion of the transfer membrane containing an electrophoretic blot while it is in a position appropriate for detection. There is also disclosed herein a process for utilizing the apparatus of the invention. In the process drying and optionally heating of the membrane where the blot has been contacted with enzyme-triggered 1,2-dioxetanes, to enhance the resulting chemiluminescent signal, is disclosed.

9 Claims, 4 Drawing Sheets

APPARATUS FOR THE HANDLING OF ELECTROPHORETIC TRANSFER MEMBRANES AND FOR THE CHEMILUMINESCENT DETECTION OF BLOTS CONTAINED THEREON

FIELD OF THE INVENTION

This invention relates to apparatus for the detection and subsequent identification of the products of gel electrophoresis and transfer blotting. More particularly it relates to apparatus for handling transfer membranes containing these products and enhancing and detecting the signal generated by suitably treated bands of separated biological materials thereon.

BACKGROUND OF THE INVENTION

Gel electrophoresis is commonly used in molecular biology to separate molecular components of a sample based on size and charge. Classically these components are transferred onto a membrane. Transfer procedures or blotting include fluid flow as in Southern blotting or electroblotting as in U.S. Pat. No. 4,589,965. The product, termed a blot, is treated to make the bands of separated molecules detectable visually or by some other detection means. For example, autoradiographic detection is used where the treatment includes radioactive labeling. Fluorescent markers, activated by a UV source, are used and detected by a two-dimensional charge coupled device as described in U.S. Pat. No. 4,874,492.

Chemiluminescence via enzymatic triggering of certain substituted 1,2-dioxetanes is a preferred method of creating a readily detectable signal. Various aspects of this art are disclosed in a number of patents.

U.S. Pat. No. 4,857,652 to Schapp discloses light producing 1,2-dioxetanes of the formula

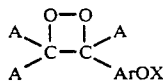

wherein ArOX is an aryl ring substituted with an X oxy group and A are passive organic groups which allow the 1,2-dioxetane to produce light when triggered by removing X. X is a chemically labile group which is removed by an activating agent. The 1,2-dioxetane compounds can be triggered to produce light at room temperatures.

U.S. Pat. No. 4,952,707 to Edwards et al., affords a general description of enzymatically-cleavable 1,2-dioxetanes. This patent describes enzymatically-cleavable chemiluminescent 1,2-dioxetanes having the formula:

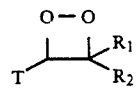

wherein $R_1$ is hydrogen, or a bond when $R_2$ is a substituent bound to the dioxetane ring through a spiro linkage, or an organic substituent that does not interfere with the production of light; $R_2$ is a fused polycyclic ring-containing fluorophore moiety having an enzymatically-cleavable, labile ring substituent; and T is a stabilizing group that prevents the dioxetane compound from decomposing before the enzymatically-cleavable labile ring substituent's bond is cleaved.

U.S. Pat. No. 4,956,477 to Bronstein et al., also describes the synthesis of enzyme-cleavable 1,2-dioxetanes, useful for chemiluminescent immunoassays, DNA probe assays, and direct assays for an enzyme.

U.S. Pat. No. 4,959,182 to Schaap describes a method and composition for providing enhanced chemiluminescence from 1,2-dioxetanes. In this method an enzyme cleavable 1,2-dioxetane is mixed with a surfactant and a fluorescent compound attached to a hydrocarbon to form a co-surfactant in a micelle or other structure. This method provides an enhancement of 500 fold in signal for enzyme-triggered chemiluminescence of 1,2-dioxetanes in solution. Moreover, Bronstein et al., (J. Biolumin. Chemilumin. 4, 99–111, 1989) report that bovine serum albumin and other water-soluble macromolecules provide a significant enhancement of chemiluminescent signal generated from enzyme-cleavable 1,2-dioxetanes in solution. All of these enhancers are believed to increase the stability of the anion intermediate and the light-emitting species by keeping them in a hydrophobic environment. However, on a hydrophobic support such as a nylon membrane, the support provides a hydrophobic environment for the anionic species. Consequently, no significant enhancement is provided by these enhancers when the enzyme is immobilized on a hydrophobic support.

AU-A36340/89 to Okada et al. describes a method for enhancing the chemiluminescent signal from enzyme-triggered 1,2-dioxetanes. The enzymatic reaction is performed at the optimum pH for the enzyme. Afterwards the pH is increased by the addition of strong base to enhance the luminescent reaction. Increases in signal from 7 to 59 fold were reported for assays done on polystyrene beads.

WO89/06650 to Bronstein et al. discusses dioxetanes for use in assays, and including a fluorescent chromophore spiro-bound at the 4-carbon of the dioxetane. The dioxetane has the formula:

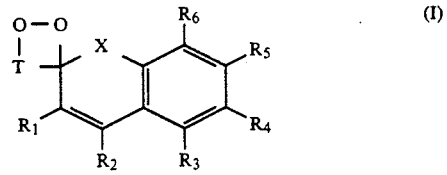

where X is $CR_7R_8$, O, S, or R-R (where each $R_7$, $R_8$, and R, independently, is H, alkyl, heteroalkyl, aryl, heteroaryl, cycloalkyl, cycloheteroalkyl, aralkyl, aklaryl, or an enzyme cleavable group). Each $R_1$, $R_2$, $R_3$, $R_4$, $R_5$, and $R_6$, independently, is H, an electron withdrawing group, an electron donating group, heteroaryl, or an enzyme cleavable group, or groups $R_1$–$R_6$ together form a ring. T is a substituted or unsubstituted aryl, polyaryl, cycloalkylidene or polycycloaklylidene group spiro-bound at the 3-carbon of the dioxetane. These dioxetanes are used in an assay to detect a member of a specific binding pair or an enzyme.

U.S. Pat. No. 4,705,847 to Hummelen et al. relates to a process for preparing substituted polycyclo-alkylidene polycyclo-alkanes, such as substituted adamantylidene adamantanes, and the corresponding epidioxy compounds. The polycycloalkylidene polycycloalkanes are halogenated, and thereafter the halogenation product is optionally subjected to a substitution reaction.

The resulting products are converted to the corresponding epidioxy compounds. Various epodioxy compounds are disclosed which contain a dioxetane ring. These compounds are useful as thermochemiluminescent labels.

U.S. Pat. No. 4,948,975 to Erwin et al., describes a quantitative luminescence imaging system which provides a means to measure low light levels from luminescent reactions in electromagnetic fields, e.g., microwave radiation, and its use in the areas of chemiluminescent assays and thermal microdosimetry. The effect of the microwave radiation on chemiluminescence described in the patent and in a publication (Kiel, Bioelectromagnetics 4, 193-204, 1983) is significantly different from the instant description. The system described involves enzymatic reactions, specifically the oxidation of luminol catalyzed by peroxidase enzymes, in protein gels which are kept wet with solution. The enhancement affected by microwave radiation is due to an increased mobility of substrate (hydrogen peroxide) within the gel.

Method and apparatus for handling and processing blot membranes during blotting, hybridization and detection is disclosed in U.S. Pat. No. 4,812,216 and related U.S. Pat. No. 4,913,791. These references disclose a method and apparatus for supporting and handling blot membranes during the course of blotting, analysis, and storage. An apparatus is disclosed including membrane support means in combination with one or more receptacles in a cooperating, releasable lock or key means so that the membrane is received in the same orientation from receptacle to receptacle. A method is also disclosed including providing a membrane and support means suitable secured to one another (such as by interlocking or adhesive) and whereby the membrane is handled conveniently by the support means without disturbing the membrane or biological material bound thereto. The membrane is transported as a single piece part arrangement to and from processing stations. However, these references do not teach an automated and controlled assembly for processing of a membrane including a biological sample, wherein the membrane is desirably contacted by a pressure head and enclosed within light shielding apparatus during the detection stage.

U.S. Pat. No. 30,595 discloses a container for dispensing reagent slides into apparatus which carry out quantitative chemical analysis of fluid samples. A generally rectangular housing includes a chamber for receiving a stack of the slides. The container fits into a complementary shaped nest in the analysis apparatus, and discontinuity means are included to inhibit insertion at an improper orientation. U.S. Pat. No. 4,152,390 discloses a chemical analyzer comprising a plurality of cartridges containing test slides. A slide transfer mechanism feed slides from a cartridge, transports them to a metering device for fluid deposit, and delivers the slides by conveyor means through an incubator and to an analysis means. However, these references do not teach the combination of guide apparatus to position a transfer membrane, a pressure head for releasable engagement, and light shielding apparatus which selectively encloses about the membrane as in the present invention.

It is an object of the present invention to provide apparatus for handling electrophoretic transfer membranes which provides and controls: means for receiving a transfer membrane and locating that membrane for detection, automatically controlled actuation of the detection means, means for membrane discharge, and means for resetting so that a subsequent transfer membrane may be processed. It is a further object of the present invention to provide apparatus useful in chemiluminescent detection wherein the chemiluminescent signal is enhanced. A feature of the present invention is the incorporation of a pressure head within the apparatus which distorts the membrane and optionally heats the membrane desirably for improved signal strength. It is an advantage of the present invention that the apparatus and the process disclosed herein enable accurate and controlled processing of electrophoretic samples with minimal involvement of skilled laboratorians. These and other objects, features, and advantages of the present invention will become apparent upon having reference to the following description of the invention.

SUMMARY OF THE INVENTION

There is disclosed according to the present invention an improved apparatus for the handling and detecting of an electrophoretic transfer membrane that comprises a rigid frame (i) that supports a flexible membrane (ii) along portions of the periphery thereof, the membrane (ii) containing thereon a detectable electrophoretic blot, and a detector therefor. The improvement comprises:

(a) guide apparatus designed to accommodate the transfer membrane so that it is positioned for engagement by pressure head (b) and for detection;

(b) pressure head positioned with respect to the guide apparatus to releasably engage the membrane (ii);

(c) light shielding apparatus positioned with respect to the guide apparatus to selectively enclose about the transfer membrane; and (d) means for sequentially operating the apparatus so that the pressure head engages the membrane (ii) while the transfer membrane is in a position appropriate for detection.

An improved process for the handling and detecting of the above described electrophoretic transfer membrane is also disclosed. The improvement comprises:

(a) positioning the transfer membrane within guide apparatus for engagement by a pressure head and for detection;

(b) engaging the membrane (ii) with a pressure head as the membrane (ii) is resident within said guide apparatus to distort the membrane (ii) from the rigid frame (i);

(c) operating light shielding apparatus positioned with respect to the guide apparatus to enclose about the transfer membrane; and (d) detecting the electrophoretic blot, during engagement of the membrane (ii) with the pressure head as in (b) and operation of the light shielding apparatus as in (c).

In a preferred embodiment, detecting the electrophoretic blot comprises:

(a) suitably treating the membrane (ii) containing thereon a detectable electrophoretic blot with enzyme-triggered 1,2-dioxetanes;

(b) drying the membrane (ii);

(c) optionally heating the membrane (ii) simultaneously with drying or thereafter; and (d) detecting the chemiluminescence of the 1,2-dioxetanes associated with the electrophoretic blot, with the drying and/or heating being conducted either prior to or simultaneously with detection.

Moreover, heating the membrane (ii) may be accomplished by heating means disposed within the pressure head.

DETAILED DESCRIPTION OF THE INVENTION

Figure 1:
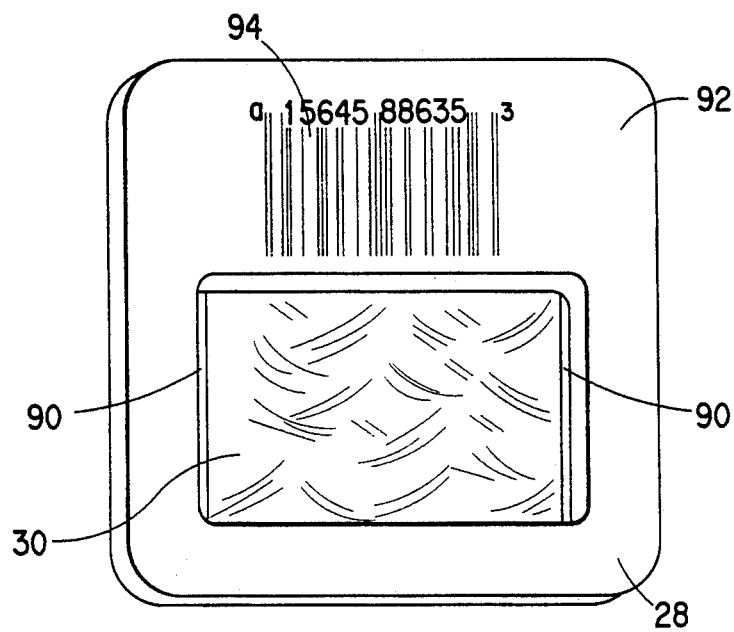
FIG. 1 is a perspective view of a transfer membrane and an associated frame.

Referring to FIG. 1, there is disclosed an electrophoretic transfer membrane comprising a rigid frame 28 that supports flexible membrane 30. Flexible membrane 30 is held mechanically, or by use of an adhesive or the like, in or on rigid frame 28. The rigid frame 28 is sized slightly larger than the width of flexible membrane 30 leaving a gap 90 on both sides so that when the electrophoretic transfer membrane is contacted by a pressure head, the flexible membrane 30 is biased from the plane of rigid frame 28. Frame 28 has an extended region 92 to facilitate handling and to provide space for identifying indicia such as bar code 94. A typical membrane or support is surface-modified nylon or the like usually on a support such as a non-woven fabric about 1.5 mm thick. Such thin membranes, while reasonably rugged, are highly flexible. Thus frame 28 lends handling stability to the membrane.

Framed membranes may be used in manual transfer procedures or, more preferably, in automated apparatus. Identification of bacterial species may be done by the method described in Webster, U.S. Pat. No. 4,717,653 in such apparatus which may include the module of this invention. Similarly, framed membranes may be supplied to the module of the instant invention acting as a stand-alone device. In either instance the invention contributes to the utility of the identification method by simplifying the task of the operator, by improving the repeatability of the procedure and, as a result of this procedural ease and because of the automation of the enhancement method described herein, greatly reducing the time for chemiluminescent detection from hours to minutes.

Figure 2:
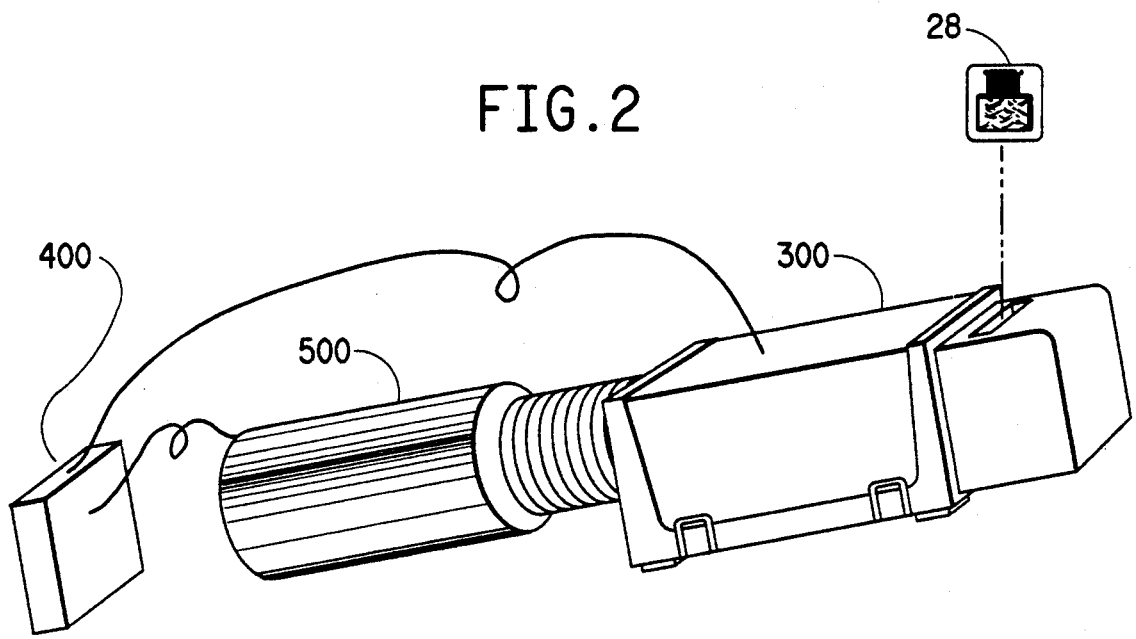
FIG. 2 is a schematic view of the components used in conjunction with the detection module of the invention.

The flexible membrane 30 mounted in rigid frame 28 and carrying a blot from a previously performed gel electrophoresis is by treatment by 1,2-dioxetanes as disclosed herein to prepare it for detection by chemiluminescence. Then it is transported as indicated in FIG. 2 to detection module 300 where it is positioned for reading by detection device 500 which is preferably a CCD camera. Data from detection device 500 is fed to process control means 400, preferably a minicomputer, where by use of a method such as that described by Hubner in U.S. Pat. No. 4,885,697 identification is done. Orderly, and properly timed processing, also is under the control of control means 400 which actuates the various motors, such as 328, to carry out the needed functions. Control means 400 also provides analytical means to carry out identification as was mentioned above.

Figure 3:
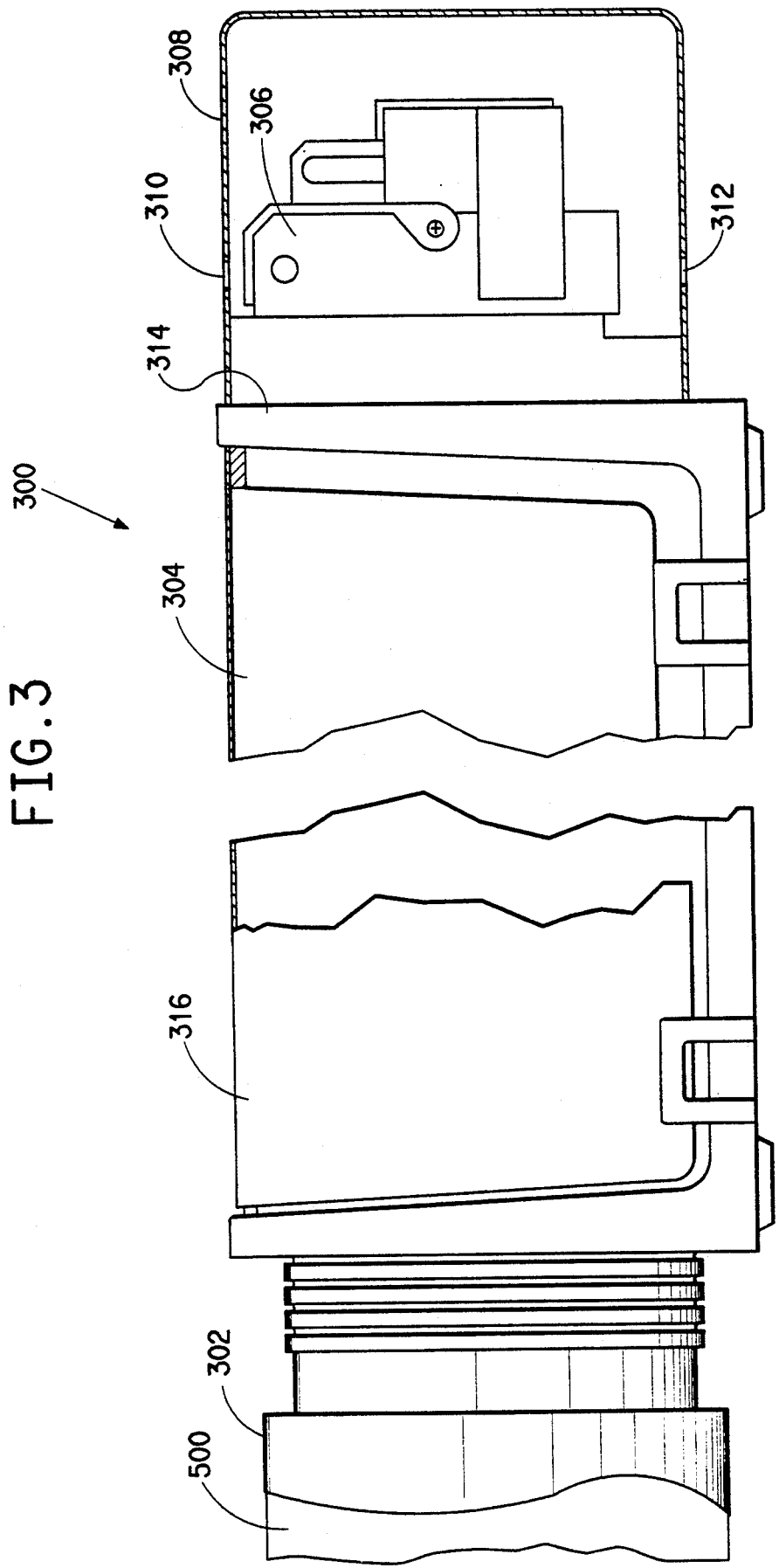
FIG. 3 is a side elevational view in partial cross-section of the detection module.

According to FIG. 3, module 300 is seen to have three main components: camera head 302 (and camera 500 which may be a CCD camera such as a Star 1/A available from Photometrics Ltd., of Tucson, Ariz.), light tube 304, and frame handling unit or escapement 306. It will be noted that no input means is shown in this figure because the module is well adapted to either manual frame-by-frame feed or automatic feed from a magazine of frames. The frame handling unit 306 is enclosed by front cover 308 which excludes light and has inlet slot 310 and outlet slot 312 for passage of frame/membrane or support components 28/30. Unit 306 is attached by means not shown to structural base 314 which with main cover 316 defines light tube 304 enclosing the optical axis between camera head 302 and a positioned membrane 30. The various components are attached one to the other by means not shown.

Module 300 has the following functions: it permits entry into the frame handling unit of a suitably framed and treated membrane ready for detection of the bands in a Southern, Northern or Western blot assay, holds the membrane at the focus of a detector (a CCD camera here) under near dark conditions, provides thermal enhancement of the chemiluminescent intensity of enzyme-activated 1,2-dioxetanes bound to the membrane, and ejects the membrane after the pattern on the membrane has been sensed by the detector and recorded, all in a controlled sequence.

Figure 4:
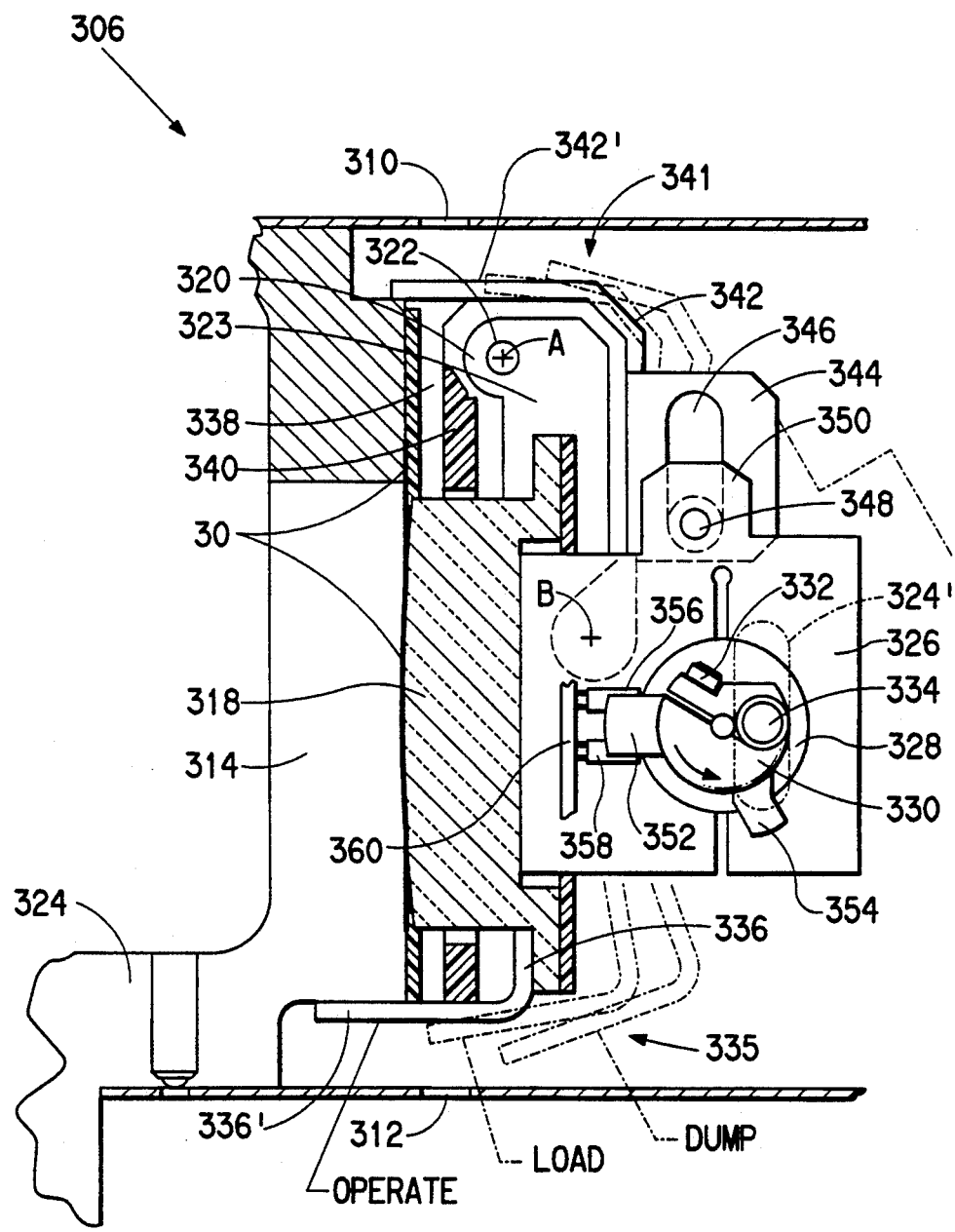
FIG. 4 is a side elevational view in cross-section of the membrane processing portion of the module.

The detailed structure of the frame handling unit is seen in FIG. 4. The guide apparatus (a) may further comprise a frame guide 340 having through slot 338 aligned to receive the transfer membrane for engagement by pressure head (b) and to discharge the transfer membrane after completion of the detection. Pressure head 318 is fastened by moment arm to 323 which rotates about axis A on pivot shaft 322 which is fixed by means not shown to structure 324 which is an extension of structure 314. In this fashion the pressure head 318 may releasably engage the flexible membrane 30. That is, the pressure head 318 engages the membrane 30 when the electrophoretic transfer membrane is positioned for detection but is released from the membrane 30 during "load" and "dump" configurations. Motor bracket 326 is fastened to pressure head 318 by means not shown and is split and bored through to mount motor 328 which may be a motor/reducer type (a gear head DC motor such as a "Maxon" No. 2322,846-11.1-12-000 Red. available from Maxon, 838 Mitten Rd, Burlingame, Calif.). Dynamic braking is provided by well known circuitry. The motor is clamped by a fastener not illustrated. Indexing cam 330 is clamped to the shaft of motor 328 by fastener 332 and mounted to it is cam follower 334 (which may be a ¼ inch STOCK DRIVE product NO. A7Y5CF2512). This is engaged in a cam slot which is on a bracket on structure 324 and, while not visible in the cross-section shown is indicated by phantom lines as 324'. Rotation of the motor in the direction of the arrow for example will swing the assembly described above through the indicated angular positions from "operate" to "load" to "dump" the configuration having been so selected. The parts are shown in the "operate" or "home" position and the other positions are indicated by partial phantom views. The light shielding apparatus (c) of the invention comprises a first light shielding means 341 located proximate to the through slot 338 in the region of reception of the transfer membrane (the top portion of FIG. 4). The apparatus (c) further comprises a second light shielding means 335 located proximate to the through slot 338 in the region of discharge of the transfer membrane (the bottom of FIG. 4). Both light shielding means 341 and 335 have "open" and "close" positions. That is, as the apparatus is positioned to receive an electrophoretic transfer membrane, the first light shielding means 341 is open sufficient to permit passage of the membrane into the through slot 338 and the second light shielding means 335 is closed sufficient to stop passage of the membrane through the through slot 338. Thus the electrophoretic transfer membrane is loaded within the assembly with the membrane 30 positioned for contact by the pressure head 318. During detection, the first and second light shielding means are located to the "operate" positions, which are sufficient to shield light to enable detection to occur. After detection, the second light shielding means 335 is opened sufficient to permit the electrophoretic transfer membrane to be discharged from the through slot.

The first and second light shielding means 341 and 335 are preferably comprised of first and second arms 342 and 336 to which are connected first and second blades 342' and 336'. The first and second blades 342' and 336' are in light shielding relationship with the through slot 338, so that the first and second light shielding means 341 and 335 may function to shield light for detection to occur. The first and second arms 342 and 336 are operably connected at the other (distal) ends thereof so that they may act for example in unison, with coordinated operate, load and dump configurations. Second arm 336 is fastened to pressure head 318, swings with it, and is shown in the home position where the second blade 336' blocks and light-seals vertical through-slot 338 against ambient light from below. The through-slot 338 is so sized and aligned with entry and exit slots 310, 312 (part of a cover) as to allow passage and processing of frames 28 and associated membranes 30. Note that in the load position first blade 342' fully clears slot 338 permitting loading but second blade 336' does not clear the slot and acts as a stop and, as it moves to the fully closed position acts to hold frame 30 in the correct vertical location.

One side of through slot 338 is made up of frame guide 340 which preferably is fabricated from an engineering plastic exhibiting good strength and low surface friction such as DELRIN TM (a product of E. I. du Pont de Nemours and Company, Wilmington, Del.). The top of through slot 338 is closed during operation by first light shielding means 341 (specifically by the first blade 342'). This pivots about axis B (see phantom lines) which is rotatably attached to structure 324 with suitable brackets not shown and carries cam plate 344 having cam slot 346. A cam follower 348, which is similar to follower 334, is attached to extension 350 of motor bracket 326 and engaged in cam slot 346. Indexing cam 330 has wide flag 352 and narrow flag 354 on its periphery. These extend sufficiently to interact with sensors 356, 358 which are mounted in the circular path of the tabs on circuit board 360 which is fastened to pressure head 318 in cavity 458 and mounts all electrical circuit components as well. Preferably, two optoelectronic sensors are used, such as an H2311 made by Harris which have a transmitter and a receiver each.

The light beam is interrupted by passage of the flags to create a control signal. Sensor 356 is the "stop" sensor—when flag 352 blocks it and "home" sensor 358, motor 328 is directed to stop in the home position or 0 degrees. Here a signal is sent to the CCD camera 500 to operate. Flag 354 is sized so that it can interrupt only one sensor at a time—it is spaced from the other flag and provides a signal indicating that the array of parts is in the "load" position, which is at 7 degrees, and a signal is sent to the external input device, if there is one, or to an indicator for an operator, to drop the next frame 28. At 13 degrees, a dump situation is provided in which the bottom of slot 338 is opened and the frame 28 is dropped out of the module under the influence of gravity.

Figure 5:
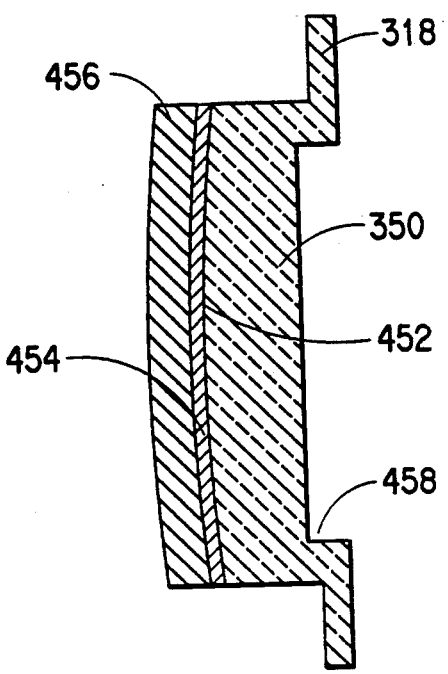
FIG. 5 is a more detailed cross-sectional view of a pressure head shown in FIG. 4.

The detailed structure of pressure head 318 is shown in FIG. 5. The basic head 350 is a part fabricated from an engineering material which is a relatively good insulator such as DELRIN TM and which on the membrane or support contacting end is shaped to pass through the aperture of frame 28. That end is formed with a curved surface 452 to which a controllable electric heater 454 is attached such as a Minco Part No. HR5435R17.9L12A with a type K foil thermocouple included in its structure. Attachment is by lamination by RTV. Similarly laminated to heater 454 is pressure plate 456 which is fabricated from aluminum or some such material which is a good thermal conductor. Pressure plate 456 further is contoured to bias the flexible membrane 30 away from rigid frame 28 during engagement. Certain electrical sheet heaters are available with metal casings and if such are used and the heat capacity is adequate, pressure plate 456 may well be eliminated.

In operation motor 328 rotates from the "dump" position (13 degrees) moving all parts pivoted from axis A on a counterclockwise arc as cam follower 334 moves in fixed cam 324'. The first arm 342, pivots clockwise about axis B forced by the arcuate motion of cam follower 348 in cam 346. At the load position (7 degree) the first blade 342' does not cover the top of through slot 338 but the tip of second blade 336' is still below through slot 338. A signal is generated by the presence of narrow flag 354 at sensor 356 the unshown external input device feeds (and drops by gravity a frame 28 through entry slot 310 into through slot 338, the frame lodging on the tip of second blade 336'. After a preselected time interval, motor 328 rotates until the wide flag 352 is in the "home" position as described where the action of the cams has moved both first and second arms 342, 336 into a light sealing relationship with through slot 338 as shown. Pressure head 318 has been moved forward so that its forward surface, pressure plate 456, contacts the back surface of membrane or support 30 and bows it out under tension through the aperture in frame 28. Heater 454, constantly energized to a preselected, controlled temperature as described, provides thermal energy to dry the membrane or support 30 and to enhance the image thereon. Camera 500 is actuated.

The image is entered into the control device 400 and processed. After a preselected time interval rotation is resumed and, at the 13 degree "dump" position, the tip of second blade 336' having been withdrawn to its maximum, frame 28 is dropped and passes through exit slot 312 to waste (not shown). The cycle may then be repeated. It will be seen now that rotary indexing cam 330 and the associated mechanical elements comprise an escapement for moving membrane frames 30 through the module.

Figure 6:
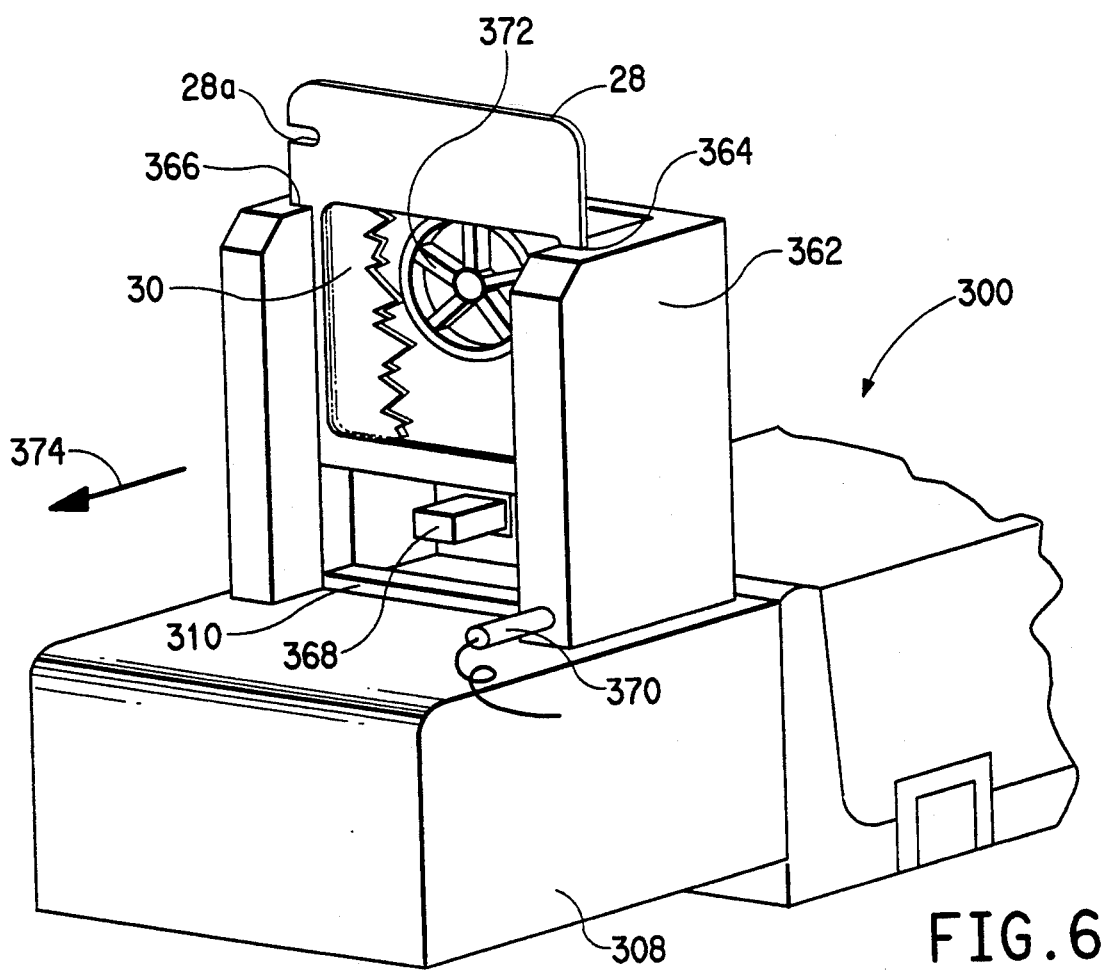
FIG. 6 is a side elevational view in cross-section of the membrane processing portion of the module.

The detection module of the invention has been described as useful in conjunction with apparatus for automated handling of the transfer membranes. In the embodiment of FIG. 6 such a module is adapted to stand alone operation with manual feeding of transfer frame 28. Referring now to FIG. 6, there is seen a partial perspective view of such a detection module 300. Front cover 308 is modified to accommodate manual feeding assembly 362 which is fastened by means not shown to structure 314. A pair of facing grooves 364, 366 are located above slot 310 in cover 308 and spaced to provide a sliding fit for frame 28. Assembly 362 is fabricated from an engineering plastic with low friction characteristics such as DELRIN TM made by E. I. du Pont de Nemours and Company, Wilmington, Del. 19898. Entry into slot 310 is releasably prevented by retractable stop 368 which is mounted to a spring-loaded linkage not seen connected to and operated by solenoid 370. A fan 372 is mounted on the back of assembly 362 so that ambient air is blown in the direction of arrow 374 intercepting a membrane 30 when its associated frame 28 is intercepted by stop 368.

In use, a laboratorian takes a membrane and frame 30, 28 carrying a separated (blot) pattern, which has been prepared for detection (a procedure which renders the pattern chemiluminescent - lysis, isolation, digestion or lysis, deproteinization, digestion), and drops it into slot 364, 366 so that the bottom of frame 28 rests on stop 368. Control device 400 is actuated. Fan 364 blows air on membrane 30 removing excess moisture which remains on the membrane from the preceding processing. After a controlled time period, a signal from device 400 actuates solenoid 370 and stop 368 is withdrawn permitting frame 28 to drop through slot 310. After this, processing is as described above and the operator need not intervene further until the spent membrane and frame 30, 28 is dropped out of slot 312 in cover 308 and the identification is presented by the control apparatus.

The detection module 300, and the method of enhancement incorporated therein, has been described in terms of identification of micro-organisms as by the method of Webster. Other applications (employing suitable associated apparatus and methodology) should be apparent to those skilled in the art. These include determination of proteins using Western Blotting, ELISAs, and RNA analysis using Northern Blotting.

Drying the membrane before detection, regardless of the method used, produces a 4–6 fold improvement in signal. Heat-drying in an oven gave the most consistent results, but a similar effect was observed with vacuum drying, air drying, or drying with a heat lamp. The additional effect of heating occurs when the membrane is heated during the capture of the image with, for example, a CCD camera, i.e., the membrane is heated while the picture is being taken. A dry membrane or a wet membrane can be heated during the capture of the image because the membrane dries very quickly when heated directly on a heating block. The employment of these steps is a new concept in enzyme-triggered chemiluminescence. The enhancement that is observed is obtained when carbonate buffer is used as the assay buffer. Much lower signals are obtained when one of the other common buffers for alkaline phosphatase assays, e.g., Tris, diethanolamine, and 2-amino-2-methyl-1-propanol, are used as the assay buffer.

Several combinations of drying with or without subsequent heating the sample are contemplated. Each variation on the process of the invention should be reviewed against the particular need of the researcher. Thus, drying the sample prior to detection but heating the sample during detection, and heat-drying simultaneously during detection are preferred procedures when practical. In some cases where heating during detection is not practical, e.g., detection using X-ray or photographic film, heat-drying prior to detection is a preferred approach.

Other useful combinations of heating and/or drying (and their relationship to the detection step) include drying the sample alone (without further heating once the sample is dry) prior to detection; drying the sample and then in sequence heating the sample, both prior to detection; drying the sample alone during detection (although not practical given the time involved and not favored as the signal remains constant for some time after the membrane is dry); and drying and heating the sample simultaneously with detection.

By "drying" the solid support containing the sample it is meant that residual solvent or other aqueous solution is removed from the sample. Without intending to be bound by any particular theory, one possible explanation for the beneficial effects of drying in the process that has been advanced is that the sample (typically a membrane) is free of solvent molecules that can collide with the excited molecules, so that less energy is lost to collision dissipation resulting in an increase in quantum efficiency. Solvent molecules are removed by drying, which eliminates collisional quenching of the chemiluminescence. Drying the membrane before detection results in a 4-fold to 6-fold increase in signal strength over conventional techniques in which the membrane is kept wet with substrate solution. The membrane must be completely dry to realize the full enhancement effect.

In the drying step of the process, the solid support is introduced for a suitable time and temperature to a procedure selected from the group consisting of vacuum drying, convection drying, air drying, the use of microwave energy, and the use of electrical energy. Thus, when drying by vacuum system about 15 to 30 minutes at ambient temperature is sufficient. Convection drying (using for example conventional ovens) is accomplished in about 5–30 minutes at 30°-100° C. Air drying is concluded in 30 minutes or longer (several hours) duration at ambient temperature. Drying depends on a number of parameters, e.g., the size of the membrane, the composition of the membrane, and the initial wetness of the membrane. The drying conditions will need to be optimized for every application. The conditions that are given were developed for nylon membranes, 8×8 cm in size or smaller that are blotted before drying to remove excess solution.

For drying the membrane, the selection of drying method is governed by convenience. The only requirement is that the membrane is thoroughly dried. A preferred procedure is electrical heating of wet or previously dried membranes during detection with a CCD camera. The electrical heater 454 of pressure head 318 accomplishes this purpose. Also to some extent the fan 372 contributes to the drying function. The optimum conditions will depend on the application. For some applications, producing the highest signal in the shortest time interval may be desirable. This would require using a high temperature, e.g., 100° C. It may be desirable to have a more sustained emission using a lower temperature, e.g., 70°-80° C., so that multiple exposures of varying length can be taken. In this way, higher concentration lanes are read at shorter exposures, while lower concentration lanes are read at longer exposures. This approach increases the dynamic range of the system.

By "heating" the sample it is meant that after the removal of solution from the sample, heat or other energy is applied to the sample to raise the temperature therein. Without again intending to be bound by any particular theory, one possible explanation for the beneficial effects of heating in the process that has been advanced is that heating appears to decompose the intermediate molecules quicker and/or more completely, resulting in a more intense signal gathered over a much shorter time as opposed to conventional techniques not applying heat measures. In the process, heating is accomplished by introducing the solid support for a suitable time and temperature to any of a variety of procedures which can be incorporated into the apparatus herein, such as electrical heating (as by continued application of electrical heater 454 in pressure head 318).

In electrical heating during detection with a previously dried membrane, the membrane is dried in a convection oven for 10-30 minutes at 40° C. Then the membrane is heated by electrical heater 454 at 40°-100° C. for 30 seconds to 10 minutes while the signal is measured using a CCD camera. A series of images is taken, typically 30 seconds to 2 minutes, and the image that gives the best signal to background ratio is selected.

Heating is typically conducted for 1-10 minutes at 40°-100° C. Heating may also be viewed as one way to dry the membrane. There is a distinction between drying the membrane before detection, by whatever means, and heating either a wet or dry membrane during detection. It is believed that if the membrane is not heated during detection, the main effect that is observed is one of drying, regardless of the drying method employed. Heating during detection provides the greatest enhancement effect.

It is readily appreciated that the drying and heating techniques disclosed herein are well understood according to those skilled in the art, and further that the listed techniques are intended to be merely representative and not exhaustive of all techniques available for purposes of the presently claimed process.

It also can be readily appreciated that the various drying and heating techniques disclosed herein may be optimized to suit a particular need of the researcher.

The enhanced chemiluminescent detection process of this invention is applicable to enzyme-based solid-phase assays which utilize 1,2-dioxetane substrates producing semi-stable intermediates. As the process is more specifically applied to well accepted chemiluminescent 1,2-dioxetane systems, reference is made to the disclosures of U.S. Pat. No. 4,931,223 and U.S. Pat. No. 4,952,707, both incorporated by reference herein. There are also numerous publications that describe the use of enzyme-triggered 1,2-dioxetanes for enzyme immunoassays (Bronstein et al., J. Biolumin. Chemilumin. 4, 99-111, 1989, Southern Blotting (Bronstein et al., BioTechniques 8, 310-314, 1990), and DNA sequencing (Tizard et al., Proc. Natl. Acad. Sci. 87, 4514-4518, 1990).

Such assays are based upon the use of specific binding interactions of one molecule by another. Specific binding partners include: antibody-antigen, complementary nucleic acid strands, binding protein-vitamin, and binding protein-nucleic acid. One member of the binding pair is disposed of and immobilized in some way on a solid support. The support is then incubated in a solution containing the second member of the binding pair, which is either directly labeled with an enzyme or which has attached a binding group, e.g., biotin or avidin, that can subsequently bind the enzyme label. In the latter case, the support is incubated in a solution containing the enzyme label. The support is then incubated in a solution containing the appropriate 1,2-dioxetane substrate for the enzyme label used. For example, 3-(2'-spiroadamantane)-4-methoxy-4-(3"-phosphoryloxy)-phenyl-1,2-dioxetane can be used when alkaline phosphatase is the enzyme label and 3-(2'-spiroadamantane)-4-methoxy-4-(3"-$\beta$-D -galactopyranosyloxyphenyl)-1,2-dioxetane can be used when $\beta$-D-galactosidase is the enzyme label. Some of the more common assays include enzyme-linked immunosorbent assays (ELISAs), DNA probe assays, and Southern Blotting.

The enzymatic reaction removes the enzyme-cleavable group from the 1,2-dioxetane, forming an anionic intermediate. The half-life of this intermediate is several hours when it is adsorbed onto a hydrophobic support, such as a nylon membrane. The intermediate decomposes by rupture of the dioxetane ring, forming two carbonyl compounds. At least one of these compounds is formed in an electronically excited state, which deactivates with the emission of radiant energy. An example of the reactions involved is as follows:

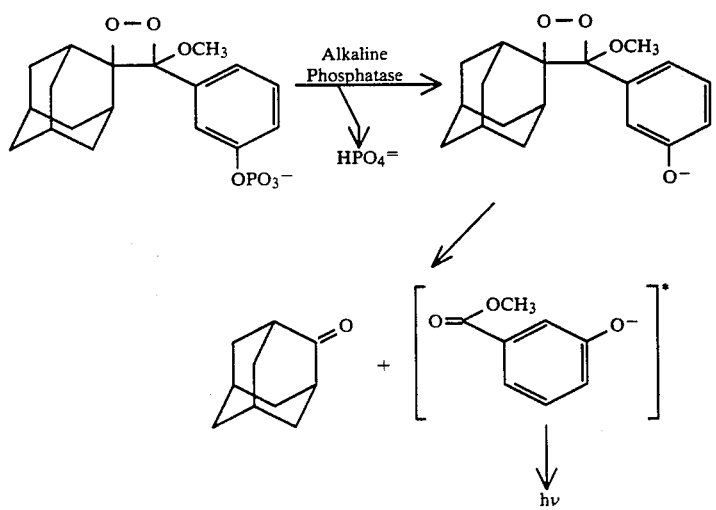

The drying and optional heating steps are carried out on the solid support after the incubation in substrate solution, and the chemiluminescent signal is measured, as described earlier. Heating the support provides an additional increase in the chemiluminescent signal, possibly by triggering the decomposition of the intermediate anion.

Preferred solid supports are hydrophobic and include, for example, nylon membranes, polymer beads, and microtiter plates and are used in the assay to separate bound from unbound enzyme label. The selection of solid support is a function of the type of assay being performed. Polymer beads and microtiter plates are typically used for immunoassays, although membranes can also be used. A membrane must be used in any assay that requires a transfer from an electrophoresis gel, i.e., Southern, Western, and Northern blots. The most commonly used solid supports are polymer beads, microtiter plates and membranes. However, the support can really be any shape, e.g., tubes and paddles. A hydrophobic support is preferred because it provides a hydrophobic environment which presumably stabilizes the anionic 1,2-dioxetane intermediate. It is theorized that with hydrophilic supports enhancement would be substantially less because the intermediate would decay more rapidly.

A complimentary binding partner of the substance is immobilized on a solid support. For example, if the target on the support is DNA, a complimentary DNA probe is used. For an immunoassay, an antibody-antigen pair is used. A second binding partner can be directly labeled with enzyme, or it can be modified to contain a second binding substance that will subsequently bind the enzyme label. In the present system, target DNA is immobilized on the membrane. The binding partner used is a complimentary DNA probe that has been modified to contain the vitamin biotin. After hydridization, in which the complimentary DNA strands anneal, an avidin-alkaline phosphatase conjugate is added. Avidin is a binding protein that has a strong affinity for biotin. Therefore, the complexation of biotin and avidin attaches the enzyme label to the DNA probe. Alkaline phosphatase is used when the 1,2-dioxetane is 3-(2'-spiroadamantane)-4-methoxy-4-(3"-phosphoryloxy) phenyl-1,2-dioxetane (commonly referred to as AMPPD). Additionally β-D-galactosidase is used when the 1,2-dioxetane is 3-(2'-spiroadamandane)-4-methoxy-4-(3"-β-D-galacto-pyranosyloxy-phenyl)-1,2-dioxetane (commonly referred to as AMPGD).

The measurement of chemiluminescent signal intensity is performed by any of various techniques readily appreciated and understood by those skilled in the art. The methods vary as much as the purposes for which the present process may be used. Thus, detection enhancement may be useful for several applications including increasing the sensitivity in solid phase assays such as ELISAs and DNA probe assays. Other assays include Southern, Northern, and Western analyses. The enhancement process of this invention is useful for imaging nucleic acid or protein blots, in which case X-ray film is commonly employed. The primary advantage of the present enhancement process is that it greatly reduces the time required for the detection process, i.e., substrate incubation time plus detection of the chemiluminescent signal. A detection procedure that would take several hours can be done in 10 minutes or less. Other equipment useful at the measurement stage include X-ray or photographic film and accompanying components, photomultiplier tubes, and electronic imaging detectors (such as charge-coupled device (CCD) cameras). Having the capability to capture the image quickly and at great intensity avoids other engineering problems such as camera cooling and background noise levels.

What is claimed is:

1. In an improved apparatus for the handling of an electrophoretic transfer membrane and the detecting of a signal generated by separated biological materials on said electrophoretic transfer membrane that are suitably treated to generate said signal, wherein the electrophoretic transfer membrane comprises a rigid frame (i) that supports a flexible membrane (ii) along portions of the periphery thereof, the membrane (ii) containing thereon a detectable, signal generating electrophoretic blot, and a signal detector therefor, the improvement comprising:
   (a) guide apparatus designed to accommodate the rigid frame (i) and the flexible membrane (ii) so that the flexible membrane (ii) is positioned for reading in a location for detection while engaged by pressure head (b);
   (b) pressure head positioned with respect to said guide apparatus and said location to releasably engage the flexible membrane (ii);
   (c) light shielding apparatus positioned with respect to said guide apparatus to selectively enclose about the rigid frame (i) and the flexible membrane (ii); and
   (d) means for sequentially operating said guide apparatus (a), said pressure head (b), and said light shielding apparatus (c) so that the rigid frame (i) and the flexible membrane (ii) are enclosed and said pressure head engages the flexible membrane (ii) while the transfer membrane is in said location appropriate for detection.

2. The apparatus of claim 1 wherein said guide apparatus (a) further comprises a frame guide having a through slot aligned to receive the rigid frame (i) and the flexible membrane (ii) for engagement of said flexible membrane (ii) by said pressure head (b) and to discharge the rigid frame (i) and the flexible membrane (ii) after detection.

3. The apparatus of claim 1 wherein said pressure head is pivotally positioned with respect to said guide apparatus to releasably engage the flexible membrane (ii), via a moment arm rotatably secured to the apparatus.

4. The apparatus of claim 3 wherein said pressure head further comprises a pressure plate which contacts the flexible membrane (ii) and is shaped to bias the flexible membrane (ii) away from the rigid frame (i) during engagement, and optionally heating means secured to said pressure plate, said pressure plate and optional heating means being secured to said moment arm.

5. The apparatus of claim 2 wherein said through slot has first and second ends with said location for detection therebetween and said first end is in a region of reception of the rigid frame (i) and the flexible membrane (ii) and said second end is in a region of discharge of the rigid frame (i) and the flexible membrane (ii) and said light shielding apparatus comprises a first light shielding means located proximate to said first end of said through slot and having open and close positions, and a second light shielding means located proximate to said second end of said through slot and having open and close positions, operably connected so that as the rigid frame (i) and the flexible membrane (ii) are received within said through slot said first light shielding means is open and said second light shielding means is closed sufficient to stop the rigid frame (i) and the flexible membrane (ii) from passing thereby, during detection said first and second light shielding means are closed sufficient to shield light for detection, and as the rigid frame (i) and the flexible membrane (ii) are discharged from said through slot, said second light shielding means is open.

6. The apparatus of claim 5 wherein said first light shielding means comprises a first arm with a first blade at one end thereof in light shielding relationship to said through slot, and said second light shielding means comprises a second arm with a second blade at one end thereof in light shielding relationship to said through slot, and said first and second arms being operably connected at each other end thereof.

7. The apparatus of claim 6 wherein said guide apparatus (a) further comprises a cover having opposed entry and exit slots which accommodate the rigid frame (i) and the flexible membrane (ii), said entry slot being located proximate to said first end of said through slot with said first light shielding means interposed therebetween and said exit slot being located proximate to said second end of said through slot with said second light shielding means interposed therebetween.

8. In an improved apparatus for the handling and detecting of an electrophoretic transfer membrane that comprises a rigid frame (i) that supports a flexible membrane (ii) along portions of the periphery thereof, and the membrane (ii) containing thereon a detectable electrophoretic blot, the improvement comprising in combination:

(a) guide apparatus designed to accommodate the rigid frame (i) and the flexible membrane (ii) so that the flexible membrane (ii) is positioned for reading in a location for detection while engaged by pressure head (b);

(b) pressure head positioned with respect to said guide apparatus and said location to releasably engage the flexible membrane (ii);

(c) light shielding apparatus positioned with respect to said guide apparatus to selectively enclose about the rigid frame (i) and the flexible membrane (ii);

(d) means for sequentially operating said guide apparatus (a), said pressure head (b), and said light shielding apparatus (c) so that the rigid frame (i) and the flexible membrane (ii) are enclosed and said pressure head engages the flexible membrane (ii) while the transfer membrane is in said location appropriate for detection; and (e) means for detecting the signal generated by the electrophoretic blot comprising a CCD camera focused upon the flexible membrane (ii) in said location while the flexible membrane (ii) is engaged by said pressure head, and with respect to said guide apparatus so that a suitable image of the signal generated by the blot is obtained during engagement of the flexible membrane (ii) by the pressure means.

9. The apparatus of claim 8 wherein a light excluding tube is interposed between said CCD camera and said guide apparatus (a) to establish focusing of a suitable image of the signal generated by the blot.

* * * * *